United States Patent [19]

Fahim

[11] 4,339,438

[45] * Jul. 13, 1982

[54] INJECTABLE MALE ANIMAL STERILANT FOR SELECTIVELY CONTROLLING THE FUNCTION OF TESTES

[75] Inventor: Mostafa S. Fahim, Columbia, Mo.

[73] Assignee: The Curators of the University of Missouri, Columbia, Mo.

[*] Notice: The portion of the term of this patent subsequent to May 29, 1996, has been disclaimed.

[21] Appl. No.: 42,550

[22] Filed: May 25, 1979

Related U.S. Application Data

[62] Division of Ser. No. 651,712, Jan. 23, 1976, abandoned, and Ser. No. 757,099, Jan. 5, 1977, Pat. No. 4,156,427.

[51] Int. Cl.³ .................. A61K 31/70; A61K 33/30
[52] U.S. Cl. .................................. 424/145; 424/180; 424/289
[58] Field of Search ................. 424/180, 145, 289

[56] References Cited

U.S. PATENT DOCUMENTS

| | | | |
|---|---|---|---|
| 1,690,175 | 11/1928 | Paterson | 424/145 |
| 3,219,527 | 11/1965 | Gurney | 424/28 |
| 3,803,308 | 4/1974 | Zipper | 424/130 X |
| 3,887,704 | 6/1975 | Licherstein | 424/145 |
| 3,923,982 | 12/1975 | Lamand et al. | 424/145 X |
| 4,156,427 | 5/1979 | Fahim | 128/215 |

Primary Examiner—Leonard Schenkman
Attorney, Agent, or Firm—Grace J. Fishel

[57] ABSTRACT

An injectable chemical compound capable of producing sterility in male animals having scrotal testes for use in selectively controlling the exocrine function of the testes in the production of sperm and the endocrine function in the production of testosterone. Said injectable chemical compound being a physiologically acceptable astringent, preferably a water soluble zinc compound, a tannin or combinations thereof. Various concentrations of said compound being selectively injected directly into the testes or into the scrotum to suppress spermatogenesis and, optionally, to suppress production of testosterone.

11 Claims, 2 Drawing Figures

INJECTABLE MALE ANIMAL STERILANT FOR SELECTIVELY CONTROLLING THE FUNCTION OF TESTES

This is a Division of Application Ser. No. 651,712 filed Jan. 23, 1976, now abandoned and of application Ser. No. 757,099 filed on Jan. 5, 1977 now U.S. Pat. No. 4,156,427.

BACKGROUND OF THE INVENTION

1. Field of the Invention

This invention relates generally to the field of drug, bio-affecting and body treating compositions, and more specifically to physiologically acceptable astringents for use in selectively controlling the exocrine function of the testes in the production of sperm and the endocrine function in the production of testosterone.

2. Description of the Prior Art

A large number and variety of chemical approaches have been tried to affect spermatogenesis in male animals. These approaches have included luteinizing hormones, testosterones, steroids and other steroidal derivatives. Examples of such compounds are described in U.S. Pat. No. 3,836,640.

In nearly all of these prior approaches, the compounds have been administered orally or injected into the body. None have proved chemically or commercially successful. Nearly all have failed because of adverse side effects or reduction of libido.

The spermicidal effects of many non-essential metal are also known and have been comprehensively reported. Gunn, Samuel A. and Thelma Clarke Gould. 1970. The Testis, Vol. III, Influencing Factors, 377–481. Many of the metals studied are normally considered as toxic in any form.

The presence of zinc in the male reproduction process is well established, but its mode of action is not clearly defined. Human seminal plasma normally contains a high concentration of zinc. Gallob-Hausmann, Gerda. Zinc and Its Physiological Relationship to the Human Body—A Review. However, there are indications that zinc ions under certain conditions can exert toxic effects on human spermatozoa. White, I. G. 1955. The Toxicity of Heavy Metals to Mammalian Spermatozoa. Austral. J. Exp. Biol. 33, 359–366. Rosado, A., et al. 1970. Inhibition of Human Sperm Motility by Calcium and Zinc Ions. Contraception 2, 259–273. Kesserü, E., et al. 1972. Influence of Metals in In Vitro Sperm Migration in the Human Cervical Mucus. Contraception 6, 231–240.

Zinc evidently plays a role in reproduction, appearing with carbonic anhydrase and alkaline phosphatase in the prostate and testes. The amount of zinc found in this tissue, however, is much higher than would normally be associated with the amount of these two enzymes present. Despite the large number of experiments demonstrating the presence and behavior of zinc in the male sex accessory organs, the function of this metal remains obscure. Byar, David P. 1974. Zinc in Male Sex Accessory Organs: Distribution and Hormonal Response, Chapt. 6, Male Accessory Sex Organs—Structure and Function in Mammals.

The toxic effects of zinc ions on human spermatozoa in vitro have also been studied. Lindholmer, C. 1974. Toxicity of Zinc Ions to Human Spermatozoa and the Influence of Albumin. Andologia 6 (1), 7–16. The purpose of this study was to analyze the effects of zinc on the motility and survival of human spermatozoa, and to what extent these effects could be modified by albumin. Collected sperm cells were separated from the seminal fluid by centrifugation and washed in a special solution. The washed cells were divided into two sample groups and 4% human albumin added to one group. A total concentration of 4% albumin was chosen because this corresponds to the total protein concentration of human seminal fluid.

The test results showed that the addition of zinc at a concentration of 5 $\mu$g/ml (0.075 mM) to the samples without albumin markedly inhibited sperm motility. By contrast, the addition of zinc at a concentration of 50 $\mu$g/ml (0.75 mM) to the samples containing 4% albumin only slightly inhibited sperm motility. The protective effect of the albumin thus was clearly demonstrated.

It is presumed that with the concentration of albumin and zinc normally present in human semen, zinc albumin complexes are formed, some of which may precipitate on the cell surfaces. The biological significance of such precipitate and coating complex is not known, but is assumed to be of importance for protecting the cells against toxic substances in the seminal fluid.

SUMMARY OF THE INVENTION

The present invention is directed to the in vivo chemical control of spermatogenesis and the control of testosterone production in male animals having scrotal testes. This control is provided by the direct injection of a physiologically acceptable astringent into the testes or scrotum.

The effective control of spermatogenesis in the manner taught by this invention is accomplished without the undesirable side effects observed in the methods of the prior art.

DETAILED DESCRIPTION OF THE INVENTION

Figure 1:
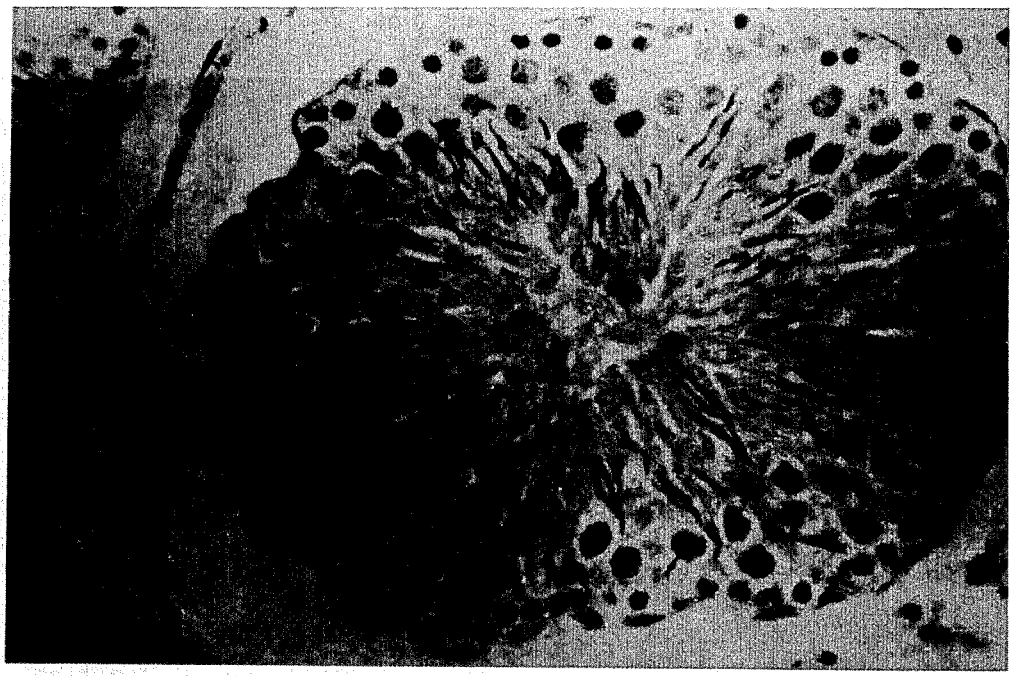

The degree that spermatogenesis and testosterone production are inhibited depends upon the locus of the injection and upon the nature and amount of the astringent. In some cases, it is desirable to inhibit sperm production without affecting the production of testosterone. By a proper selection of astringent and place of injection, it is possible to stop sperm production without significantly affecting the interstitial cells which produce testosterone. It is the production of this male hormone which controls the animal's disposition, sex characteristics and libido.

Suitable astringents are water soluble and are selected from those materials which precipitate proteins. When injected into the testes or scrotum, they must be capable of selectively inhibiting spermatogenesis and the production of testosterone. They must also be physiologically acceptable and produce no undesirable toxic effects.

Such astringents if injected in the scrotum cause tanning of the *tunica albuginea*. Temperature regulation of the testes is interfered with by this hardening of the tunica which surrounds the testes. Since sex cells are susceptible to injury by a temperature equaling that of the interior body, such treatment provides a method for control of sperm production. In addition to hardening the tunica, some of the astringent penetrates the testes and has the same effect as if injected therein. Such effect, however, is relatively less since most of the astringent does not pass therein.

If injected into the testes, suitable astringents, on the cellular level, cause degeneration of the sex cells in the seminiferous epithelium. This occurs through disintegration of the nuclear and cytoplasmic membranes of the sex cells. It is caused perhaps because the astringents disrupt the chemistry of the testicular fluid between the tubules and cause the tubules to have a hostile environment for the development of sex cells. Depending upon the severity of treatment, the sex cells are progressively affected beginning at the lumen and extending to the periphery of the tubules. Preferably the Sertoli cells and basement membrane of the tubules are left intact, however, under very severe conditions, these are also affected.

If all of the sex cells are destroyed, the treatment is irreversible and results in the complete cessation of sperm production. If some of the sex cells are left, however, it is possible that the epithelium will regenerate and sperm production eventually resume.

In general, a smaller amount of astringent is necessary to stop sperm production if it is injected directly into the testes than if it is injected into the scrotum. Hence by selecting the dose and the locus of the injection, the sex cells can be selectively destroyed thus controlling the exocrine function of the testes in the production of sperm.

By selecting the dose and locus, the endocrine function can also be controlled. For example, it is possible by the present treatment to stop sperm production without affecting the Leydig cells in the stroma between the tubules. If it is desired to reduce the production of testosterone, it is possible to affect the Leydig cells by increasing the dose. This effect may be accomplished with a lesser amount if the astringent is injected directly into the testes.

The male hormone testosterone plays a vital role in the development of the male animal and controls the secondary sex characteristics, sex impulse and proper maintenance of the genital ducts and accessory glands. The present treatment provides a means for stopping sperm production without otherwise affecting the male, the size of his genitals or his libido. The present treatment optionally provides a means for complete castration if it is desired to stop the production of testosterone as well as the production of sperm. This may be desired, for example, for the purpose of changing the animal's disposition or for the purpose of shrinking his sex organs.

Most of the astringents for use as described above are tannins, zinc salts or combinations thereof. Suitable zinc salts include zinc acetate, zinc chloride and zinc sulfate. When the astringent is tannic acid, it is preferably predissolved in water and the insoluble precipitate of gallic acid separated therefrom by filtration. If a combination of tannic acid and zinc salt is used, it is preferred that an equal stoichiometric amount of each be used. So mixed, as injected, the effective astringent is zinc tannate said injectable chemical sterilant preferably containing the zinc sulfate in an amount from about 5 mg to 125 mg as zinc sulfate heptahydrate and contains the tannin in an amount from about 2 mg to 125 mg as tannic acid.

It is preferred that the astringent solution be buffered to a pH from about 4.0 to about 6.5. This is because the pH of the solution affects the absorption and distribution of the drug throughout the scrotum and the testes. While such buffering is also desirable to avoid discomfort to the subject in the form of a stinging sensation, it is not necessary.

Before the astringent is injected, the scrotum should be cleaned with a disinfectant and the needle cleaned before the injection of each testis. This is because the testes are very susceptible to infection.

The selected testis is palpated and the head and tail of the epididymis located. The injection is then given into the midline of the testis. It is important that the injection not be given near the head of the epididymis so that the blood vessels are avoided as they enter the testis. If the injection is given into the blood vessels, the astringent coagulates the blood and forms a clot. It is also important that the injection not be given in the tail of the epididymis. This is because the astringent causes granuloma in fully matured sperm. When one testis has been injected, the other testis is palpated and an injection made into its midline.

The nerves in the testes follow the blood vessels but endings within the tubules seem doubtful. In any case, injection into the scrotum or into the testes does not cause the animal great discomfort.

The volume of the injection, however, does affect the subject's comfort. This is not so critical when the injection is into the scrotum but is highly critical when the injection is into the testes. If too large a volume is injected into the testes, the tubules are ruptured and the subject experiences pain.

The exact amount which can be injected depends, as aforementioned, on the locus of the injection as well as on the species of the animal and size of the particular subject's genitals. The proper amount in each case can be easily determined in view of the examples set forth below.

Figure 2:

The following examples and accompanying drawings illustrate the invention. In the drawings, FIG. 1 is a light micrograph showing a histological section of a control rat testes; and FIG. 2 is a similar view after treatment with zinc sulfate.

EXAMPLE 1

This example illustrates the effect of zinc sulfate on male reproduction of sexually mature rats when administered orally.

Three hundred sexually mature rats were divided into three groups, Group I being a control. Group II rats were treated daily with 15.0 mg $ZnSO_4.7H_2O$ and Group III rats with 50.0 mg, both groups receiving said treatment for 30 days.

As shown in Table 1, the data indicate no significant change in the weight of the testes, epididymis, prostate or seminal vesicles. No histological changes were observed in the male reproductive organs and no change in growth rate was observed.

As shown in Table 2, no significant zinc concentration was found in the blood and liver and no change was noted in testosterone levels.

TABLE 1

ZINC ADMINISTERED ORALLY
Male Rats

| Treatment | Initial Body Wt. gm | Final Body Wt. gm | Testes gm | Epididymis gm | Prostate gm | Seminal Vesicles gm |
|---|---|---|---|---|---|---|
| Control | 224.4 ± 5.75 | 411.1 ± 15.02 83.3% | 3.06 ± 0.10 | 0.91 ± 0.03 | 0.44 ± 0.01 | 0.76 ± 0.05 |
| 15 mg ZnSO₄ orally for 30 days | 211.7 ± 3.77 | 365.6 ± 5.06 72.7% | 2.88 ± 0.17 | 0.94 ± 0.03 | 0.44 ± 0.03 | 0.73 ± 0.04 |
| 50 mg ZnSO₄ orally for 30 days | 223.5 ± 3.59 | 408.7 ± 27.13 82.9% | 2.94 ± 0.13 | 0.91 ± 0.04 | 0.42 ± 0.02 | 0.78 ± 0.04 |

TABLE 2

ZINC ADMINISTERED ORALLY
Male Rats

| Treatment | Zn p.p.m. in 1 gm dry liver | Zn p.p.m. in 24-hr. urine collection | Zn μg/ml in serum | Testosterone ng/ml serum | μM PCA 1 g Liver | Liver gm |
|---|---|---|---|---|---|---|
| Control | 77.29 ± 1.68 | 11.81 ± 0.35 | 2.13 ± 0.28 | 7.76 ± 0.67 | 2.40 ± 0.11 | 18.27 ± 0.91 |
| 15 mg ZnSO₄ orally for 30 days | 84.16 ± 1.86 | 29.75 ± 10.57 | 2.35 ± 0.19 | 6.25 ± 1.68 | 2.23 ± 0.26 | 14.19 ± 0.30 |
| 50 mg ZnSO₄ orally for 30 days | 79.65 ± 1.35 | 48.58 ± 7.68 | 2.00 ± 0.08 | 6.57 ± 0.58 | 2.63 ± 0.22 | 16.75 ± 0.66 |

ZnSO₄ solution was made up from ZnSO₄ . 7H₂O salt. Therefore 15 and 50 mgZnSO₄ . 7H₂O correspond to 8.42 mg, 28.07 mgZnSO₄.

EXAMPLE 2

This example illustrates the effect of zinc sulfate on male reproduction of sexually mature rats when administered intraperitoneally.

Four hundred sexually mature rats were divided into four groups, Group I being a control. The rats in Groups II, III and IV were treated daily for 30 days, respectively, with 0.5, 1.0 and 5.0 mg ZnSO₄.7H₂O. At the end of 60 days, as in Example 1, the rats were sacrificed.

As shown in Table 3, there was no significant reduction in the weight of the testes, epididymis, prostate or seminal vesicles and no histological changes were observed in the sex organs as compared to the control.

There was, however, a significant reduction in the rate of gain but the testosterone level was not changed. A higher concentration of zinc was found in the liver as shown in Table 4, but the zinc concentration in the testes, epididymis, prostate and seminal vesicles was substantially the same as in the control.

TABLE 3

ZINC ADMINISTERED INTRAPERITONEALLY
Male Rats

| Treatment | Initial Body Wt. gm | Final Body Wt. gm | Testes gm | Epididymis gm | Prostate gm | Seminal Vesicles gm |
|---|---|---|---|---|---|---|
| Control (H₂O injected) | 208.8 ± 4.6 | 406.2 ± 9.07 94.5% | 2.68 ± 0.15 | 0.78 ± 0.07 | 0.47 ± 0.02 | 0.87 ± 0.19 |
| 0.5 mg ZnSO₄ injected for 30 days | 216.4 ± 1.05 | 3.88 ± 6.37 *79.7% | 2.94 ± 0.03 | 0.90 ± 0.02 | 0.42 ± 0.04 | 0.72 ± 0.04 |
| 1.0 mg ZnSO₄ injected for 30 days | 219.4 ± 3.5 | 392.4 ± 10.1 *78.9% | 3.05 ± 0.07 | 0.90 ± 0.02 | 0.46 ± 0.03 | 0.74 ± 0.04 |
| 5.0 mg ZnSO₄ injected for 30 days | 215.7 ± 2.2 | 352.3 ± 12.6 *63.3% | 2.74 ± 0.13 | 0.88 ± 0.04 | 0.41 ± 0.02 | 0.89 ± 0.07 |

*Significant reduction of weight gain from the control (p < 0.001)

TABLE 4

ZINC ADMINISTERED INTRAPERITONEALLY
Male Rats

| Treatment | Zn p.p.m. in 1 gm dry liver | Zn p.p.m. in 24-hr. urine collection | Zn ug/ml in serum | Testosterone ng/ml serum | uM PCA 1 g liver | Liver gm |
|---|---|---|---|---|---|---|
| Control (H₂O injected) | 77.29 ± 1.68 | 11.81 ± 1.35 | 2.13 ± 0.28 | 7.76 ± 0.67 | 1.73 ± 0.15 | 17.51 ± 0.58 |
| 0.5 mg ZnSO₄ injected for 30 | | | | | | |

TABLE 4-continued

ZINC ADMINISTERED INTRAPERITONEALLY
Male Rats

| Treatment | Zn p.p.m. in 1 gm dry liver | Zn p.p.m. in 24-hr. urine collection | Zn ug/ml in serum | Testosterone ng/ml serum | uM PCA .1 g liver | Liver gm |
|---|---|---|---|---|---|---|
| days 1.0 mg ZnSO$_4$ injected for 30 | 92.71 ± 2.37 | 22.96 ± 3.40 | 2.60 ± 0.10 | 6.79 ± 1.34 | 1.86 ± 0.24 | 14.85 ± 0.48 |
| days 5.0 mg ZnSO$_4$ injected for 30 | 94.27 + 1.43 | 24.29 + 4.92 | 2.48 + 0.08 | 6.87 + 0.58 | 1.62 + 0.12 | 14.99 ± 0.64 |
| days | 134.75 ± 15.44 | 41.31 ± 8.87 | 2.88 ± 0.29 | 6.30 ± 0.68 | 1.17 ± 0.06 | 13.11 ± 0.68 |

ZnSO$_4$ solution was made up from ZnSO$_4$ . 7H$_2$O salt. Therefore 0.5 mg. 1.0 mg and 5.0 mg ZnSO$_4$ . 7H$_2$O correspond to 0.28 mg, 0.56 mg and 2.81 mg ZnSO$_4$ respectively.

EXAMPLE 3

This example illustrates the effect of zinc sulfate on male reproduction in sexually mature rats when administered into the scrotum.

One hundred sexually mature rats were divided into two groups, Group I being a control. Each of the Group II rats was injected with 25 mg ZnSO$_4$.7H$_2$O into each side of the scrotum.

As shown in Table 5, there was a significant reduction in the weight of the testes and epididymis of the treated rats. There was no difference, however, in the weight of the prostate and seminal vesicles.

Histological examination of the testes as shown in FIGS. 1 and 2 showed a significant change in the condition of the sex cells but no difference in the condition of the Leydig cells. This correlated with the finding that there was no significant reduction in testosterone levels as compared with the control.

Four hundred sexually mature male rats were divided into four groups, Group I being a control. The rats in Groups II, III and IV were treated by injecting 0.5, 2.5 and 5.0 mg ZnSO$_4$.7H$_2$O into the testes. Such injection was made into the midline of each testis with a sterilized needle.

The results of this example showed a significant reduction in the weight of the male reproductive organs, particularly in that of the testes and prostate. The amount of reduction increased with the dose administered and was correlated with a decrease in the testosterone level.

All of the animals from Examples 1–5 were mated with females in heat. Those rats which were treated orally (Example 1) or intraperitoneally (Example 2) with zinc sulfate impregnated the females. Pregnancy also occurred from those animals which had received 0.5 and 2.5 mg ZnSO$_4$.7H$_2$O in the vas deferens while those animals treated with 5.0 mg did not impregnate

TABLE 5

ZnSO$_4$—7H$_2$O INJECTED INTO SCROTUM

| Treatment* | Body Weight gm | Liver Weight gm | Testes gm | Epididymis gm | Prostate gm | Seminal Ves gm |
|---|---|---|---|---|---|---|
| Control 0.25 ml H$_2$O injected into each scrotum | 428.0 ± 10.0 | 13.26 ± 1.13 | 3.57 ± 0.13 | 1.23 ± 0.04 | 0.80 ± 0.09 | 0.98 ± 0.61 |
| 0.25 ml ZnSO$_4$ 7H$_2$O 25 mg injected into each scrotum | 431.2 ± 17.2 | 13.53 ± 0.87 | *1.42 ± 0.09 | *0.56 ± 0.06 | 0.82 ± 0.06 | 1.20 ± 0.02 |

*Animals were sacrificed 60 days after treatment
*Significantly different from the control (P < 0.001)

EXAMPLE 4

This example illustrates the effect of zinc sulfate on male reproduction of sexually mature rats when administered in the vas diferens.

Eighty sexually mature male rats were divided into four groups, Group I being a control. The rats in Groups II, III and IV were treated by injecting 0.5, 2.5 and 5.0 mg ZnSO$_4$.7H$_2$O into the vas diferens.

At the end of 60 days, as in the other examples, the rats were sacrificed. There was no significant change in the weight of the testes, prostate or seminal vesicles and no effect on spermatogenesis. There was an increase in the weight of the epididymis, however, in the Group IV rats due to the development of sperm granulomas.

EXAMPLE 5

This example illustrates the effect of zinc sulfate on male reproduction of sexually mature rats when administered in the testes.

the females due to sperm granuloma of the epididymis (Example 4). No pregnancy resulted from any of the rats treated in Examples 3 and 5. Only Examples 3 and 5 are in accordance with the present invention. Examples 1, 2 and 4 were conducted for the purpose of comparison.

EXAMPLE 6

This example illustrates a treatment wherein spermatogenesis is stopped without reducing the weight of the testes. This is desired, for example, by some pet owners and usually when the subject is a human male.

Ninety sexually mature male rats were divided into two groups, Group I being a control. The rats in Group II were treated by injecting 0.05 ml into each testis of a drug, herein called Kastrin and containing about an equal amount of zinc sulfate and tannic acid, more particularly containing in this instance 0.25 mg of tannic acid and 0.25 mg of ZnSO$_4$.7H$_2$O.

All of the animals were mated with a female in heat. None of the treated rats impregnated the females. When the rats were sacrificed, it was found that there was no significant difference in the weight of the reproductive organs and that the testosterone levels were not significantly different from the control group.

EXAMPLE 7

As in Example 6, 90 sexually mature rats were divided into two groups, Group I being a control. The rats in Group II were injected with a mixture of zinc sulfate and tannic acid such that 2.5 mg of tannic acid and 2.5 mg of $ZnSO_4.7H_2O$ was injected into each testis.

The treated rats in Group II were sterile, had smaller testes but there was no change in the testosterone levels as compared to the control group.

EXAMPLE 8

As in Examples 6 and 7, 90 sexually mature rats were divided into two groups, Group I being a control. The rats in Group II were injected with a mixture of zinc sulfate and tannic acid such that 5.0 mg of tannic acid and 5.0 mg of $ZnSO_4.7H_2O$ was injected into each testis.

The treated rats in Group II were sterile, had smaller reproductive organs and lower testosterone levels as compared to the control animals. More particularly, the testosterone level of Group I was $8.2 \pm 0.46$ ng/ml as compared to less than 1 ng/ml in the treated animals.

All of the treated animals in Examples 6, 7 and 8 were kept for a year with no mortality. When they were sacrificed, none had abnormal organs, liver, kidney, adrenal, lung or pituitary and no toxic side effect was noted whatsoever.

EXAMPLE 9

As in the previous examples, sexually mature rats were divided into two groups, Group I being a control. The Group II rats were injected with a mixture of zinc sulfate and tannic acid such that 5.0 mg of tannic acid and 5.0 mg of $ZnSO_4.7H_2O$ was injected into each side of the scrotum into the cavity of the tunica vaginalis.

The treated rats in Group II were sterile and were kept for a year with no mortality. When they were sacrificed, there was no reduction in the weight of the prostate or in the testosterone levels as compared to the rats in the control.

When the results of this example are compared with those in Example 8, it is seen that the effect on the endocrine function of the testes is more pronounced when the injection is into the testes as compared to the scrotum.

EXAMPLE 10

The rats in this example were divided and treated as in Example 9 except that the amount of tannic acid and zinc sulfate injected into each side of the scrotum was doubled.

As in Example 9, all of the treated rats were sterile. When the rats were sacrificed, however, there was found a reduction in the weight of all of the reproductive organs and a significant reduction in the testosterone levels in the blood.

Thus it is seen that the same effect on the testes can be had by injecting an astringent into the scrotum or into the testes. The amount necessary to achieve a reduction in the endocrine function, however, is more when the drug is injected into the scrotum.

EXAMPLE 11

Six dogs weighing 15 to 22 kg and aging between 8 and 11 years were injected in each testis with 1.0 ml of a mixture containing 100.0 mg of tannic acid and 100.0 mg of $ZnSO_4.7H_2O$. Before treatment, two of the dogs were diagnosed with hyperplasia of the prostate, the others with adenocarcinoma. Diagnosis was achieved by rectal and abdominal palpation and by prostate biopsy. All had difficulties in urination.

Each dog was examined weekly. After one month, the prostate was shrunk in size and the animal was able to urinate normally. Thus, surgical castration was made unnecessary and avoided.

This example shows that by controlling the endocrine function of the testes in their production of testosterone a chemical method is provided for the treatment of the prostate. In human males, as in dogs, chronic prostatitis, benign hyperplasia and adenocarcinoma of the prostate are common diseases. The present treatment provides a convenient, relatively risk free, alternative to surgery.

EXAMPLE 12

Two hundred 30-day old male rats, just weaned, were divided into four groups, Group I being a control. The rats in Group I were injected with 0.05 ml of water into each testis. The rats in Group II were similarly injected with 5.0 mg of $ZnSO_4.7H_2O$, those in Group III with 5.0 mg of tannic acid and those in Group IV with a mixture (Kastrin) containing 2.5 mg tannic acid and 2.5 mg $ZnSO_4.7H_2O$.

The data from this example are reported in Table 6. Forty of the animals were sacrificed 60 days after treatment. The others were watched for a year. The results showed that all of the treated rats were sterile. There was no significant change in the rate of gain.

TABLE 6

| Treatment | Initial Body Wt. (gm) *Wt. Gain | Final Body Weight (gm) | Liver Weight (gm) | Testes Weight (gm) | Epididymis Weight (gm) | Prostate Weight (gm) | Seminal Vesicles Wt. (gm) |
|---|---|---|---|---|---|---|---|
| | | | Effect of Kastrin in Weaned Rats | | | | |
| Control | $81.3 \pm 4.6$ 242%* | $276.1 \pm 18.6$ | $10.59 \pm 0.42$ | $2.69 \pm 0.07$ | $0.80 \pm 0.02$ | $0.23 \pm 0.02$ | $0.25 \pm 0.02$ |
| Group II | $81.3 \pm 5.4$ 229%* | $267.3 \pm 14.7$ | $9.95 \pm 0.54$ | $0.21 \pm 0.04$ | $0.10 \pm 0.03$ | $0.05 \pm 0.02$ | $0.05 \pm 0.02$ |
| Group III | $86.7 \pm 3.8$ 212%* | $270.9 \pm 15.4$ | $10.40 \pm 0.43$ | $0.46 \pm 0.12$ | $0.31 \pm 0.07$ | $0.13 \pm 0.05$ | $0.14 \pm 0.04$ |
| Group IV | $82.3 \pm 3.2$ 225%* | $267.7 \pm 11.2$ | $11.32 \pm 0.33$ | $0.21 \pm 0.02$ | $0.19 \pm 0.02$ | $0.06 \pm 0.02$ | $0.06 \pm 0.02$ |

*Rate of Gain

EXAMPLE 13

Thirty-eight litter mate dogs, 8 weeks old, were divided into four groups. The dogs in Group I were a control and were injected with 0.2 ml of water into each testis. The animals in Group II were similarly treated in each testis with 20.0 mg of tannic acid buffered to a pH of 6.5. Those in Group III were treated with 20 mg of $ZnSO_4.7H_2O$ and those in Group IV with a mixture of 10 mg of tannic acid and 10 mg of $ZnSO_4.7H_2O$.

None of the treated animals impregnated females when they reached the age of sexual maturity. There were no significant differences, however, in the rate of growth, development of the urinary tract or development of the pelvic bones as documented by x-ray. In fact, the dogs in Group II which were treated with tannic acid showed better muscular appearance than those in the control group.

Two years after treatment, all of the dogs in Groups II, III and IV were healthy, active and showed no adverse side effects whatsoever. The only difference between them and those in the control was that the treated dogs were sterile and had smaller testes. There was, however, no difference in libido.

EXAMPLE 14

Fifty sexually mature dogs were divided into two groups. Twenty, each weighing less than 15 kg, were injected in each testis with 0.5 ml of an aqueous mixture containing 2.5 mg of tannic acid and 2.5 mg of $ZnSO_4.7H_2O$. The remaining dogs, each weighing between 20 and 35 kg, were injected in each testis with 1.0 ml of a mixture containing 5.0 mg of tannic acid and 5.0 mg of $ZnSO_4.7H_2O$.

Before treatment, the semen of each dog was evaluated. On average, the volume was 5.5 ml, the motility 4+, the sperm count $400 \times 10^6$/ml, the pH 6.2 and the morphology 4% with coiled tails and 2% tailless with 8 to 10% dead.

Forty eight hours after treatment, the semen of each dog was again evaluated. On average, the volume was 5.5 to 6.0 ml, the motility 1+, the sperm count $400 \times 10^6$/ml, the pH 6.3 and the morphology 70% with coiled tails and 20% tailless with 100% dead. After one week, the volume was 4.0 ml, the motility 0, the sperm count $10 \times 10^6$/ml, the pH 6.2 and the morphology 96% with coiled tails and 4% tailless with 100% dead.

The semen of each dog was evaluated again after two weeks, one month, three months, six months, one year and two years. In each case, no live sperm were found.

Needle testicular biopsies were taken before treatment, ten months after and two years after. Histological examination showed the absence of spermatogenesis after treatment as compared to the normal condition existing before.

EXAMPLE 15

Sexually mature dogs were treated in this example as in Example 14 except that they were injected in each testis with 0.1 ml of a solution containing 5.0 mg of tannic acid and 5.0 mg of $ZnSO_4.7H_2O$.

One week after treatment, the sperm count dropped from $400 \times 10^6$ to $1-5 \times 10^6$/ml. Six months after treatment, the sperm count had recovered somewhat to $10 \times 10^6$/ml. At the end of two years, the sperm count was substantially normal. Other dogs which had been repeatedly injected with the same amount of the drug were made permanently sterile.

This example illustrates that by controlling the dose, the exocrine function of the testes can be inhibited temporarily. It also illustrates that a dose insufficient to cause permanent sterility if administered only once can induce permanent sterility if administered several times.

EXAMPLE 16

Thirty sexually mature cats weighing $4.3 \pm 0.2$ kg were divided into three groups, Group I being a control. Those animals in Group I were injected in each testis with 0.1 ml of water. Those in Group II were injected with 10.0 mg of tannic acid buffered to a pH of 6.8 and those in Group III with 5.0 mg of tannic acid and 5.0 mg of $ZnSO_4.7H_2O$.

Before treatment and after in the case of the control group, the average sperm count was $230 \times 10^6$/ml. One week after treatment, the sperm count for the animals in Groups II and III was zero.

All of the animals were observed for one year and bred with female cats in the spring and fall. None of the treated animals impregnated the females. The testosterone level for the cats in Group I was $6.8 \pm 0.2$ ng/ml, for those in Group II $4.1 \pm 0.3$ ng/ml and less than 1 ng/ml for those in Group III.

The cats in Groups I and II acted normally but those in Group III exhibited no normal male aggressiveness. The urine of Group III also lacked characteristic odor. None of the animals in Groups II or III gained any more weight than those in Group I. In other words, the treated animals did not become obese like surgically castrated animals.

EXAMPLE 17

Ten purebred Angus bulls weighing an average of 400 pounds were divided into five groups, Group I being a control. Each animal in Group I was injected with 5.0 ml of water in each testis. Those in Group II were surgically castrated. The animals in Group III were injected with 500.0 mg of tannic acid, those in Group IV with 500.0 mg of $ZnSO_4.7H_2O$ and those in Group V with 250.0 mg of tannic acid and 250.0 mg of $ZnSO_4.7H_2O$.

The animals were fed concentrate and grazed. After one year, they were sacrificed. All of the animals passed federal inspection for consumption by humans.

As shown in Table 7, all of the animals in Groups III, IV and V had a faster rate of gain than the surgically castrated animals in Group II. The animals in Group V had better carcass quality than that of any other group. No significant concentrations of zinc or tannic acid were found in the muscle, blood, spleen, heart, liver or kidney of the treated animals as compared to Groups I and II.

The data therefore indicate that the present treatment provides a safe means for castrating cattle, which in some instances provides better rate of gain and carcass quality as compared to surgical castration.

TABLE 7

| TREATMENT | BODY WEIGHT | | Rate of Gain | % Protein | % Fat |
| --- | --- | --- | --- | --- | --- |
| | Initial | Final | | | |
| Group I | 384 | 960 | 1.79 lbs/day | 17.0 | 24.0 |
| Group II | 498 | 912 | 1.29 lbs/day | 18.1 | 19.5 |
| Group III | 376 | 826 | 1.40 lbs/day | 18.3 | 18.0 |
| Group IV | 414 | 910 | 1.54 lbs/day | 17.9 | 20.9 |
| Group V | 406 | 1062 | 2.04 lbs/day | 17.7 | 22.5 |

In addition to the above, the present treatment can be used on male sheep, pigs, horses and other similar mammals having scrotal testes, including human males.

Recommended dosages, as above mentioned, depend upon the size and species of the animal and upon the desired result. Recommended dosages for sterilization of adult dogs weighing less than 10 kg is 0.25 ml into each testis of a mixture containing between 10.0 and 25.0 mg of tannic acid and 25.0 mg of $ZnSO_4.7H_2O$. For dogs weighing between 10 and 15 kg, the recommended dose is 0.5 ml into each testis of a mixture containing between 10.0 and 50.0 mg of tannic acid and 50.0 mg of $ZnSO_4.7H_2O$. For those dogs weighing between 16 and 20 kg, the recommended dose is 1.0 ml into each testis of a mixture containing between 50.0 and 100.0 mg of tannic acid and between 75.0 and 100.0 mg of $ZnSO_4.7H_2O$. For dogs weighing over 20 kg, the recommended dose is 1.0 ml in each testis of a mixture containing between 50.0 and 125.0 mg of tannic acid and 125.0 mg of $ZnSO_4.7H_2O$.

In the case of puppies between 6 and 8 weeks of age, the recommended dose is 0.05 ml into each testis of a mixture containing 2.0 mg of tannic acid and 5.0 mg of $ZnSO_4.7H_2O$. For puppies over 8 weeks but not sexually mature, the dose is preferably 0.08 ml into each of the testes of a mixture containing 7.0 mg of tannic acid and 7.0 mg of $ZnSO_4.7H_2O$. For adult cats, the recommended dose is 0.1 ml into each testis of a mixture containing 10.0 mg of tannic acid and 10.0 mg of $ZnSO_4.7H_2O$.

When tannic acid and zinc sulfate are administered in each testis in the above-mentioned recommended amounts, the treatment has been found effective to arrest spermatogenesis. Since zinc is normally present in seminal fluid, such treatment adds a minimum of foreign material to the body of the animal. Moreover, the drug remains substantially localized in the immediate area of the injection. When the astringent is zinc sulfate, for example, there is some diffusion of the zinc to the epididymis and prostate, but no diffusion beyond that. When the astringent is a combination of a zinc compound and a tannin, there is even less tendency for the zinc to diffuse. Such combinations are, for that reason, preferred.

Most of the experimental work reported in the above examples was performed by injection of the drugs with a needle. It is to be understood that other means of subcutaneous penetration may also be employed as desired.

In view of the above, it will be seen that the several objects of the invention are achieved and other advantageous results attained. More particularly, a chemical compound and treatment is taught whereby the exocrine and endocrine function of the testes are controlled.

As various changes could be made in the above described compounds and treatment without departing from the scope of the invention, it is intended that all matter contained in the above description or shown in the accompanying drawings shall be interpreted as illustrative and not in a limiting sense.

What is claimed is:

1. A sterile solution in unit dosage form for injection into the testes or scrotum of male animals having scrotal testes, said solution comprising a mixture of a water soluble physiologically acceptable zinc salt and a water soluble physiologically acceptable tannin, said zinc salt being present in an amount equivalent to the amount of zinc ion present in from about 5 mg to 125 mg of zinc sulfate heptahydrate and said tannin being present in an amount equivalent to from about 2 mg to 125 mg of tannic acid, said solution being buffered to a pH from about 4.0 to about 6.5.

2. The solution according to claim 1 wherein the zinc salt and tannin are dissolved in water.

3. The solution according to claim 2 wherein the water soluble zinc salt and the tannin are present in substantially stoichiometrical amounts.

4. The solution according to claim 2 wherein the water soluble zinc salt is a member selected from the group consisting of zinc acetate, zinc chloride and zinc sulfate.

5. The solution according to claim 4 wherein the tannin is tannic acid.

6. The solution according to claim 5 wherein the water soluble zinc salt is zinc sulfate.

7. The solution according to claim 6 wherein the tannic acid is substantially free of any gallic acid impurity.

8. The solution according to claim 7 for use with adult dogs wherein the zinc sulfate is present as zinc sulfate heptahydrate and wherein the zinc sulfate heptahydrate and tannic acid are present in a volume from about 0.25 ml to about 1.0 ml for injection into each testis.

9. The solution according to claim 7 for use with puppies between 6 and 8 weeks wherein the zinc sulfate is present as zinc sulfate heptahydrate and wherein the zinc sulfate heptahydrate and tannic acid are present in a volume about 0.05 ml for injection into each testis.

10. The solution according to claim 7 for use with puppies over 8 weeks of age but not sexually mature wherein the zinc sulfate is present as zinc sulfate heptahydrate and wherein the zinc sulfate heptahydrate and tannic acid are present in a volume about 0.08 ml for injection into each testis.

11. The solution according to claim 7 for use with adult cats wherein the zinc sulfate is present as zinc sulfate heptahydrate and wherein the zinc sulfate heptahydrate and tannic acid are present in a volume about 0.1 ml for injection into each testis.

* * * * *